United States Patent [19]

Prieels et al.

[11] Patent Number: 4,726,948
[45] Date of Patent: Feb. 23, 1988

[54] ANTI-BACTERIAL FEEDSTUFF COMPOSITIONS AND PROCESS FOR PREPARING THE SAME

[75] Inventors: Jean-Paul H. P. Prieels, Brussels; Jean-Paul Perraudin, Dilbeek, both of Belgium

[73] Assignee: Oleofina, S.A., Brussels, Belgium

[21] Appl. No.: 757,104

[22] Filed: Jul. 19, 1985

[51] Int. Cl.$^4$ .................. A61K 37/50; A61K 33/00; A61K 33/48
[52] U.S. Cl. .................. 424/94.4; 424/129; 424/130; 514/867; 426/648; 426/658
[58] Field of Search .................. 424/94, 129, 130; 514/867; 426/648, 656

[56] References Cited

U.S. PATENT DOCUMENTS 4,320,116  3/1982  Bjorck .................. 424/129
4,477,432  10/1984  Hardie .................. 424/85

OTHER PUBLICATIONS

Chem. Abst., 87:19344h, 1977.

*Primary Examiner*—J. R. Brown
*Assistant Examiner*—John W. Rollins, Jr.
*Attorney, Agent, or Firm*—John K. Abokhair; Mark A. Montgomery; M. Norwood Cheairs

[57] ABSTRACT

An anti-bacterial composition capable of being activated in the gastro-intestinal tract of mammals is provided. Said composition comprises an effective amount of lactoferrin and lactoperoxidase, and an activating system present in sufficient amounts to activate said lactoperoxidase in the gastro-intestinal tract. In accordance with another aspect of the present invention, the anti-bacterial composition is introduced into the gastro-intestinal tract of mammals as a component of foodstuff and/or animal feedstuff. In accordance with yet another aspect of the present invention, a method for treating gastro-intestinal infections is disclosed. This method for treating gastro-intestinal infections in mammals comprises introducing the above anti-bacterial composition into the intestinal tract of mammals.

25 Claims, No Drawings

ANTI-BACTERIAL FEEDSTUFF COMPOSITIONS AND PROCESS FOR PREPARING THE SAME

FIELD OF THE INVENTION

The present invention relates to new anti-bacterial compositions which additionally have beneficial nutritional effects. More particularly, the present invention relates to foodstuff and/or animal feedstuff containing said anti-bacterial compositions. Additionally, the present invention relates to the preparation of the anti-bacterial compositions and to their use in pharmaceutical products.

BACKGROUND OF THE INVENTION

The present invention relates to foodstuff and animal feedstuff comprising an anti-bacterial composition, said composition exerting an anti-bacterial effect in the gastro-intestinal tract of said animals. The present invention also relates to feedstuff which have a beneficial effect on animal growth.

It is well known that domestic animals and particularly young animals, are susceptible to contracting severe gastro-intestinal infections which mainly result from infections of *E. coli* and different species of Salmonella. Heretofore known methods to eliminate these infections include either the administration of antibiotics with the inherent risk of forming bacterial species which are resistant to antibiotics, or vaccination which is relatively expensive.

U.S. Pat. No. 4,320,116 to Bjorck discloses an anti-bacterial system comprising a thiocyanate, a solid water-soluble peroxide donor and lactoperoxidase. However, it was noted that the utilization of this lactoperoxidase system does not combat diarrhea which is common in young animals, particularly during the first weeks of life. An increase in the lactoperoxidase concentration to combat this detriment, did not result in significant improvement.

Accordingly, there is a need for an anti-bacterial system which reduces intestinal infections in animals particularly during the first weeks of life, while additionally improving the weight gain in such animals.

SUMMARY OF THE INVENTION

An object of the present invention is to provide an anti-bacterial composition effective in the treatment of gastro-intestinal infections.

Another object of the present invention is to provide animal feedstuff containing said anti-bacterial compositions.

Another object of the present invention is to provide pharmaceutical products containing said anti-bacterial compositions.

It has been unexpectedly found that the use of both lactoperoxidase and lactoferrin in the feed of young animals, has a synergistic effect in preventing and/or curing these bacterial gastro-intestinal infections.

In accordance with one aspect of the present invention, an anti-bacterial composition is provided, which composition comprises lactoperoxidase, lactoferrin, a thiocyanate, and a hydrogen peroxide precursor.

In accordance with another aspect of the present invention, the above mentioned anti-bacterial composition is incorporated into foodstuff and animal feedstuff.

In accordance with yet another aspect of the present invention, the above mentioned anti-bacterial composition is incorporated into pharmaceutical products.

DETAILED DESCRIPTION OF THE INVENTION

The key aspect of the present invention is the utilization of both lactoperoxidase and lactoferrin in an anti-bacterial composition. The use of lactoperoxidase in an anti-bacterial composition is described in U.S. Pat. No. 4,320,116 to Bjorck entitled FOODSTUFFS, ANIMAL FEEDING STUFFS AND PHARMACEUTICAL PREPARATIONS CONTAINING AN ANTI-BACTERIAL SYSTEM, which is hereby incorporated by reference in its entirety. Lactoferrin is an iron-binding protein normally found in milk, saliva, tears, and intestinal and respiratory secretions that interferes with the iron metabolism of bacteria. It has been unexpectedly found that the use of both lactoferrin and lactoperoxidase in an anti-bacterial composition gives synergistic results not obtained if either of these components is utilized alone.

The preferred use of the present invention is as an anti-bacterial composition that is activated in the gastro-intestinal tract of the treated animal. A preferred method or means for activation is the utilization of a thiocyanate and a hydrogen peroxide precursor or donor. The anti-bacterial composition may be combined with foodstuff or animal feedstuff for inroduction into the gastro-intestinal tract of humans or animals. In the alternative, the anti-bacterial composition of the present invention may be used in pharmaceutical products such as pills for oral administration or suppositories.

In a preferred method, the anti-bacterial composition of the present invention is added to animal feedstuff. It was found that when a mixture of both lactoperoxidase and lactoferrin is added to animal feedstuff in an amount of about 90 mg of mixture per kg of feedstuff, unexpected anti-bacterial results are obtained as compared to using either component alone. The utilization of the mixture reduces the occurrence of diarrhea to about a third of that observed when lactoferrin alone is used and to about a half of that observed when lactoperoxidase alone is used. Additionally, it was observed that the utilization of both lactoperoxidase and lactoferrin in animal feedstuff had a beneficial effect on the weight gain of the animals. This effect is independent of the anti-diarrhic effect and is better than that observed when each component was used alone. As a matter of fact, the use of lactoferrin alone in animal feedstuff has no effect on the weight gain of such animals.

While the present invention will hereinafter be described in terms of additives to animal feedstuff, it should be understood that the description is equally applicable to the addition of the anti-bacterial composition to human foodstuff.

The amounts of lactoferrin and lactoperoxidase present in the animal feedstuff may very within wide limits depending on the animal feedstuff used. Generally, lactoperoxidase is used in an amount of from about 2 to about 20 mg/l and preferably from about 8 to about 12 mg/l of milk substitute while lactoferrin is used in an amount of of from about 40 to about 120 mg per liter and preferably from about 60 to about 80 mg per liter of milk substitute. The lactoperoxidase in the feedstuff must be activated. The preferred activating system comprises a thiocyanate and a hydrogen peroxide precursor or donor. Generally, the thiocyanate is added to the feedstuff in an amount of at least 16 parts per million by weight based on the feedstuff, said amount being calculated as sodium thiocyanate (NaSCN).

The hydrogen peroxide precursor or donor is added in an amount sufficient to produce a sufficient amount of hydrogen peroxide to oxidize the sodium thiocyanate present. Suitable hydrogen peroxide precursors or donors include ascorbic acid-copper system, glucose-glucoseoxidase, and water soluble peroxide donors such as alkalipercarbonates, earth alkali peroxides, and carbamide peroxides.

When using milk substitute as the animal feedstuff, the thiocyanate is added in an amount from about 10 to about 100 mg per liter of milk substitute. The thiocyanate and hydrogen peroxide precursor or donor are added in an amount such that from about 10 to about 100 ppm of $OSCN^-$ are produced over a period of time of about 30 minutes.

The amounts of the different ingredients hereabove given are such that in the intestinal tract, the thiocyanate concentration is at least 0.1 mM, the hydrogen peroxide donor or precursor concentration in the intestinal tract, expressed as $H_2O_2$, is at least 0.1 mM and the lactoperoxidase/lactoferrin mixture, whether taken in a purified form and/or taken in the form of a milk product containing the mixture is at least 45 mg per liter of milk substitute. As a hydrogen peroxide precursor or donor, the glucose-glucoseoxidase system is preferably used. This system is introduced into the feedstuff in an amount of about 10 mg per liter. However, other hydrogen peroxide precursors and donors may be utilized and the amounts of these other hydrogen peroxide donor needed to obtain the desired amounts of hydrogen peroxide can be easily determined by those skilled in the art.

In accordance with another aspect of the present invention, a process for improving production of edible meat is provided, according to which, calves, pigs, sheep, rabits, venison and the like receive known nutritional components together with an anti-bacterial composition comprising a mixture of lactoferrin and lactoperoxidase, thiocyanate and a $H_2O_2$ precursor. The components are added in sufficient amounts such that the thiocyanate concentration in the intestinal tract is at least 0.1 mM, the $H_2O_2$ precursor being added in an amount such that its concentration in the intestinal tract, calculated as $H_2O_2$, is at least 0.1 mM, the lactoferrin/lactoperoxidase mixture concentration in the intestinal tract is at least 45 mg/liter of milk substitute.

In accordance with yet another aspect of the present invention, a method for treating gastro-intestinal infections, in mammals including humans is provided, said method comprising administering orally a therapeutically effective amount of the hereabove described anti-bacterial composition.

In accordance with still another aspect of the present invention, pharmaceutical preparations containing the hereabove mentioned anti-bacterial composition are provided. The anti-bacterial composition of the present invention may be used with any pharmaceutically suitable support.

Examples of treated animals include the above-mentioned and other domestic animals such as cats and dogs.

The necessary amounts of lactoperoxidase activators which may be used in the intestinal tract are well described in U.S. Pat. No. 4,320,116. The variables described in U.S. Pat. No. 4,320,116 are equally applicable to the present invention because the presence of lactoferrin does not affect the gastro-intestinal activation of lactoperoxidase.

It may be noted that in the case of lactoperoxidase, one unit represents the amount of lactoperoxidase which forms 1 mg of purogalline in 20 seconds, starting from purogallol, at pH 6.0 and at a temperature of 20° C.

Suitable salts of thiocyanate used are sodium, potassium, and ammonium salts. $LD_{50}$ of thiocyanate is 484 mg/kg bodyweight when injected intravenously in mice and is 764 mg/kg bodyweight when administered orally to rat.

In clinical use the compounds of the invention are administered normally orally, or rectally in the form of a pharmaceutical preparation, which contains an anti-bacterial system according to the invention in combination with a pharmaceutical carrier. The carrier may be a solid, semisolid or liquid diluent or a capsule. These pharmaceutical preparations are a further object of the invention. Usually the amount of active ingredients is between 0.1 to 99% by weight of the preparation, suitably between 2 to 50% by weight in preparations for oral administration.

In the preparation of pharmaceutical preparations containing an anti-bacterial system of the present invention in the form of dosage units for oral administration the ingredients elected may be mixed with a solid, pulverulent carrier, as e.g. with lactose, saccharose, sorbitol, mannitol, starch, as potatoe starch, corn starch, amylopectin, cellulose derivatives or gelatine, as well as with an anti-friction agent as magnesium stearate, calcium stearate, polyethylene-glycol waxes or the like, and be pressed into tablets. If coated tablets are wanted, the above prepared core may be coated with a solution of a polymer which dissolves or is permeable in the intestinal tract. To this coating a dye may be added in order to easily distinguish between tablets with different active compounds or with different amount of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch (as e.g. potatoe starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Pharmaceutical preparations containing an anti-bacterial system according to the invention are intended to be used in the treatment of bacterial infections in the gastro-intestinal tract caused e.g. by Shigella, Salmonella, *E. coli, Vibreo colera*, Pseudomonas (*Ps. pyocyanea*), Staphylococcus (*Staph. albus, aureus*), Streptococcus (*Strep. viridans, Strep. faecalis,* B-Streptococcus), and Proteus.

The present invention will be described in more detail in the following with reference to the examples below, however, without being limited thereto.

EXAMPLE 1

As animal feedstuff, milk substitute was prepared from the following ingredients:

| | |
|---|---|
| milk powder | 60 kg |
| lactoserum | 14.15 kg |
| fat | 17 kg |
| glucose | 5 kg |
| Ethoxyquine | 0.125 kg |
| choline chloride | 0.025 kg |
| minerals and vitamins emulsifiers. | 2.5 kg |

The concentrations of lactoferrin and lactoperoxidase in the milk powder were respectively 61 g. and 77 g. per 100 kg powder.

As activator of lactoperoxidase, 12.3 g of sodium thiocyanate together with 61 g. glucoseoxidase (71,000 U/g.) were added.

The ingredients were thoroughly mixed in a mixer. Water was added to the mixture to obtain a 13% aqueous solution. Said solution contained 10 mg lactoperoxidase and 80 mg lactoferrin per liter of milk substitute.

Said milk substitute was administered to calves in an amount of 3 liters per day (l/day) in the first week, 4 l/day the second week, 6 l/day the third week and 8 l/day from the fourth week on.

By way of comparison, the same amount of different mixtures were given to calves, said mixtures containing neither lactoferrin nor lactoperoxidase (mixture A), or containing 10 mg/l of lactoperoxidase only (mixture B), or containing 80 mg/l of lactoferrin only (mixture C).

The anti-bacterial effect was evaluated by measuring the number of diarrhea occurrences, while the nutritional effect was determined by measuring the weight gain of the calves. Calves were treated for a period of five weeks. The obtained results are indicated in Tables 1 and 2.

TABLE I

Anti-bacterial Effect
(number of Diarrhea occurrences expressed in % if control is taken as 100%)

| Mixture of invention | Mixture A (control) | Mixture B lactoperoxidase | Mixture C lactoferrin |
|---|---|---|---|
| 64 | 100 | 133 | 213 |

This table clearly shows the synergistic effect of both compounds of the invention.

TABLE I

| | Weight gain (g/day) | | | |
|---|---|---|---|---|
| Time (weeks) | Mixture of invention | Mixture A (control) | Mixture B lactoperoxidase | Mixture C lactoferrin |
| 3 | 193 | 26 | 153 | 90 |
| 5 | 304 | 180 | 283 | 238 |

In the present case, the synergistic effect is characteristic. It is noted that an increase of 68% with regard to the control is obtained, while the maximum obtained with products used alone is of 57% and 32% with lactoperoxidase and lactoferrin respectively.

EXAMPLE 2

The mixture described in Example 1 was administered to calves for a period of 10 weeks, in the same amounts as described in Example 1. The concentration in solid matter was gradually increased from 13 to 25% by weight between the 5th week and the 10th week.

By way of comparison, a mixture which does not contain either lactoferrin or lactoperoxidase was also used.

At the 10th week, diarrhea occurrences stopped with the mixture of the invention while it continued with the control.

Moreover, an increase of weight of 865 g/day with the mixture of the invention was noted as compared to only 755 g/day with the control.

EXAMPLE 3

The mixture described in Example 1 was given to sheep in an amount of 0.5 l/day for the first week, one l/day for the second week and 2 l/day thereafter. Similar results as those already obtained with calves were observed.

What is claimed is:

1. An anti-bacterial composition capable of being activated in the gastro-intestinal tract of mammals, said composition comprising:
   (a) an anti-bacterial effective amount of lactoferrin and lactoperoxidase wherein the weight ratio of lactoferrin to lactoperoxidase is from about 2:1 to about 60:1 respectively; and
   (b) an activating system present in sufficient amounts to activate said lactoperoxidase in the gastro-intestinal tract.

2. The composition of claim 1 when added to a nutritional composition wherein lactoperoxidase is present in an amount of from about 2 to about 20 mg/kg of total composition and wherein lactoferrin is present in an amount of from about 40 to about 120 mg/kg of total composition.

3. The composition of claim 1 when added to a nutritional composition wherein lactoperoxidase concentration is from about 8 to about 12 mg/kg of total composition and wherein lactoferrin concentration is from about 60 to about 80 mg/kg of total composition.

4. The composition of claim 1 wherein the activating system comprises a thiocyanate and a hydrogen peroxide precursor.

5. The composition of claim 4 wherein the thiocyanate and the hydrogen peroxide precursor are present in sufficient amounts to produce in the gastro-intestinal tract from about 10 to about 100 ppm of $OSCN^-$ over a period of about 30 minutes.

6. The composition of claim 1 wherein the hydrogen peroxide precursor is selected from the group consisting of glucose/glucose oxidase, ascorbic acid/copper, alkaline percarbonates, alkaline earth peroxides and carbamide peroxide.

7. A method for treating gastro-intestinal infections in mammals comprising introducing into the gastro-intestinal tract an effective amount of an anti-bacterial composition which comprises:
   (a) a sufficient amount of a thiocyanate to give a thiocyanate concentration in the gastro-intestinal tract of at least 0.1 mM;
   (b) a sufficient amount of hydrogen peroxide donor to give hydrogen peroxide concentration in the gastro-intestinal tract of at least 0.1 mM; and
   (c) lactoferrin and lactoperoxidase wherein the weight ratio of lactoferrin to lactoperoxidase is from about 2:1 to about 60:1 respectively.

8. The method of claim 7 wherein the anti-bacterial composition is introduced into the gastro-intestinal tract as a component of a composition selected from the group consisting of animal feedstuff and foodstuff.

9. The method of claim 8 wherein said animal feedstuff is milk substitute.

10. The method of claim 9 wherein the lactoperoxidase concentration is from about 2 to about 20 mg/l of milk substitute and wherein the lactoferrin concentration is from about 40 to about 120 mg/l of milk substitute.

11. The method of claim 7 wherein the hydrogen peroxide donor is selected from the group consisting of glucose/glucose oxidase, ascorbic acid/copper, alkaline percarbonates, alkaline earth peroxides and carbamide peroxide.

12. The method of claim 9 wherein the lactoperoxidase concentration is from about 8 to about 12 mg/l of milk substitute and wherein lactoferrin concentration is from about 60 to about 80 mg/l of milk substitute.

13. the method of claim 10 wherein the total lactoferrin and lactoperoxidase concentration is at least 45 mg/l of milk substitute.

14. Foodstuff composition comprising:
    (a) lactoperoxidase in an amount of at least 1 mg/kg of the total composition;
    (b) lactoferrin in an amount of at least 10 mg/kg of the total conposition;
    (c) thiocyanate in an amount of at least 16 ppm of the total composition; and
    (d) a peroxide donor in an effective amount of at least 21 ppm of the total composition.

15. The composition of claim 14 wherein the composition is incorporated into a liquid carrier selected from the group consisting of milk and equivalents thereof.

16. The composition of claim 15 wherein the lactoperoxidase concentration is from about 2 to about 20 mg/l of liquid carrier and wherein the lactoferrin concentration is from about 40 to about 120 mg/l of liquid carrier.

17. The composition of claim 14 wherein the peroxide donor is selected from the group consisting of glucose/glucose oxidase, ascorbic acid/copper, alkaline percarbonates, alkaline earth peroxides and carbamide peroxide.

18. The composition of claim 15 wherein the lactoperoxidase concentration is from about 8 to about 12 mg/l of carrier and wherein the lactoferrin concentration is from about 60 to about 80 mg/l of carrier.

19. The composition of claim 14 wherein the thiocyanate and the peroxide donor are present in sufficient amounts to, upon ingestion, produce in the gastro-intestinal tract, from about 10 to about 100 ppm of $OSCN^-$ over a period of about 30 minutes.

20. Animal feedstuff composition comprising:
    (a) lactoperoxidase in an amount of at least 1 mg/kg of the total composition;
    (b) lactoferrin in an amount of at least 10 mg/kg of the total composition;
    (c) thiocyanate in an amount of at least about 16 ppm of the total composition; and
    (d) a peroxide donor in an effective amount of at least 21 ppm of the total composition.

21. The composition of claim 20 wherein the composition is incorporated into a liquid carrier selected from the group consisting of milk and equivalents thereof.

22. The composition of claim 21 wherein the lactoperoxidase concentration is from about 2 to about 20 mg/l of liquid carrier and wherein the lactoferrin concentration is from about 40 to about 120 mg/l of liquid carrier.

23. The composition of claim 21 wherein the lactoperoxidase concentration is from about 8 to about 12 mg/l of carrier and wherein the lactoferrin concentration is from about 60 to about 80 mg/l of carrier.

24. The composition of claim 20 wherein the peroxide donor is selected from the group consisting of glucose/glucose oxidase, ascorbic acid/copper, alkaline percarbonates, alkaline earth peroxides and carbamide peroxide.

25. The composition of claim 20 wherein the thiocyanate and the peroxide donor are present in sufficient amounts to, upon ingestion, produce in the gastro-intestinal tract, from about 10 to about 100 ppm of $OSCN^-$ over a period of about 30 minutes.

* * * * *